United States Patent [19]

Chung et al.

[11] Patent Number: 5,247,023
[45] Date of Patent: Sep. 21, 1993

[54] HYDROCARBON POLYMERS CONTAINING BORANE GROUPS AT CHAIN ENDS OR IN POLYMER BACKBONE

[75] Inventors: T. C. Chung, State College; M. Chasmawala, Phoenixville, both of Pa.

[73] Assignee: The Pennsylvania Research Corporation, University Park, Pa.

[21] Appl. No.: 711,005

[22] Filed: Jun. 6, 1991

[51] Int. Cl.$^5$ ............... C08F 275/00; C08C 19/22
[52] U.S. Cl. ................................. 525/288; 525/337
[58] Field of Search ......................... 525/288, 337

[56] References Cited

U.S. PATENT DOCUMENTS

| | | | |
|---|---|---|---|
| 3,399,175 | 8/1968 | D'Alelio | 525/369 |
| 3,558,589 | 1/1971 | Bethea | 525/365 |
| 3,786,116 | 1/1974 | Milkovich et al. | 525/276 |
| 3,929,850 | 12/1975 | Streck et al. | 525/383 |
| 4,172,100 | 10/1979 | Tung et al. | 585/320 |
| 4,276,394 | 6/1981 | Kennedy | 525/245 |
| 4,316,973 | 2/1982 | Kennedy | 526/348.6 |
| 4,342,849 | 8/1982 | Kennedy | 525/333.7 |
| 4,734,472 | 3/1988 | Chung | 525/337 |
| 4,751,276 | 6/1988 | Chung | 526/158 |
| 5,057,594 | 10/1991 | Krutak et al. | 528/272 |

Primary Examiner—John Kight, III
Assistant Examiner—T. Mosley
Attorney, Agent, or Firm—Thomas J. Monahan

[57] ABSTRACT

Polymeric hydrocarbons having reactive borane groups at chain ends or in the polymer chain are described. These types of polymers can be used as intermediate materials for preparing a broad range of polymers which have functional groups located at both ends of the polymer chain (telechelic polymers). The process of preparing the borane-containing polymers involves metathesis degradation of the polymer at the double bond locations in the backbone and simultaneous functionalization of the broken chain ends by borane monomers. Depending on the nature of the borane monomer, the location of boron atoms can be controlled to be at either the chain ends (telechelic) or in the polymer backbone. The concentration of boron in the resulting polymer is related to the reaction time and the mole ratio between borane monomer and the double bonds in the starting hydrocarbon polymer. In turn, the borane groups are interconvertible to various functional groups, such as OH, $NH_2$, and halides, under mild reaction conditions. Overall, the chemistry is very general and is applicable to most hydrocarbon polymers. A wide variety of telechelic polymers are obtained.

17 Claims, No Drawings

HYDROCARBON POLYMERS CONTAINING BORANE GROUPS AT CHAIN ENDS OR IN POLYMER BACKBONE

BACKGROUND OF THE INVENTION

The present invention relates to polymeric hydrocarbon compounds having reactive borane groups at chain ends, or within the polymer chain, and methods of preparation thereof.

By way of background, telechelic polymers (i.e., polymers with functional groups at both chain ends) have proven to be a very interesting class of materials. They represent several potential uses, such as liquid rubber [Milkovich, R., et al., U.S. Pat. No. 3,786,116 (1974)]. In the past, these types of polymers were mostly prepared by terminating living polymers with suitable reagents in conjunction with the use of difunctional initiators [Tung, L. H., et al., U.S. Pat. No. 4,172,100 (1979)] [Kennedy, J. P., et al., U.S. Pat. No. 4,276,394 (1981] or functionally substituted initiators [Schulz, D. N., et al., J. Polym. Sci., Part A1, 12:153 (1984)]. The anionic, cationic and recently metathesis [Risse, W., et al., Macromolecules 22:1558 (1989)] [Crowe, W. E., et al., Macromolecules 23:3536 (1990)] living polymerizations are particularly preferred because these routes provide well-defined polymers with high degree of functional groups at both ends of the polymer chain. However, this process is very limited because only few monomers undergo living propagation.

It is known that olefins are interconvertible to other olefins in the metathesis reaction [Ivin, K. J., *Olefin Metathesis*, Academic Press, New York (1983)]. Usually, this exchange reaction is fast and reversible. In the case of polymer, with unsaturation in the polymer backbone, the metathesis reaction taking place in the backbone corresponds to a polymer chain breaking and reforming reversible processes. In most cases, the equilibrium conditions can be achieved and the average molecular weight of polymers becomes constant [Schrock, R. R., et al., Macromolecules 20:1169 (1987)]. This dynamic equilibrium has been applied in the degradation of polymer chains by mixing an unsaturated polymer with a small olefin molecular in a metathesis exchange reaction. The resulting products are low molecular weight polymers with some cyclic compounds [Hummel, A., et al., U.S. Pat. No. 3,558,589]. Streck extended the chemistry further by incorporating tis metathesis exchange reaction into the metathesis ring opening polymerization. With the use of organic silicon containing olefins in a ring opening polymerization of a cyclic olefin, the polymer with terminal silicon groups was obtained [Streck, R., et al., U.S. Pat. No. 3,929,850 (1975)]. However, the yield was generally quite low and the product usually contains some insoluble gel due to the side reactions. Moreover, the silyl end group is not a desirable intermediate as it is difficult to convert the silyl polymer to other functional polymers by simple mild chemical reactions.

Borane compounds are valuable intermediates in organic synthesis [Brown, H. H., *Organic Synthesis via Boranes*," Wiley-Interscience (1975)]. However, borane functional polymers are rare. In the past few years, a new functionalization chemistry using the intermediacy of novel borane monomers and transition metal catalysts, including Ziegler-Natta [Chung, T. C., U.S. Pat. Nos. 4,734,472 and 4,741,276)] and metathesis catalysts [Ramakrishnan, S., et al., Macromolecules 22:3181 (1989)] [Ramakrishnan, S., et al., Macromolecules 23:4519 (1990)] has been investigated. The advantages of this chemistry are (a) the stability of borane moiety to transition metal catalyst, (b) the solubility of borane compounds in hydrocarbon solvent (hexane and toluene) used in transition metal polymerizations, and (c) the versatility of borane groups, which can be transformed to a remarkable variety of functionalities. Many new functionalized polyolefin homo- and co-polymers, with functional groups located at the side chains, have been obtained based on this chemistry.

Borane containing polymers, with the borane groups located in the polymer backbone or at the ends of polymer chains, are very rare. One report [Chujo, Y., et al., Macromolecules 24:345 (1991)] has shown the polyhydroboration of $\alpha,\omega$-dienes and monoalkylborane to relatively low molecular weight polymer with borane groups located in the polymer chain. The compositions of the products are limited by the availability of $\alpha,\omega$-dienes. The spacer between two borons in polymer chain usually is quite small, less than 10 methylene units. On the other hand, the preparation of borane terminated polymer is very difficult. Only one example related to telechelic polyisobutylene [Kennedy, J. P., U.S. Pat. Nos. 4,316,973 and 4,342,849] has been shown. In this case, the process was very complicated, involving low temperature living polymerization of isobutylene with difunctional initiator and subsequent multiple step polymer modification.

The present invention overcomes the above-described disadvantages and limitations inherent with various borane-containing polymers and their methods of preparation. The invention presents new polymers having borane groups at the ends of their polymer chains, or within the chains, and methods of synthesis thereof.

The present invention describes polymeric hydrocarbons having a reactive borane group at chain ends or in the polymer chain. In addition, the polymer composition can cover most known hydrocarbon backbones and the borane groups can be extended to the less expensive borane compounds, such as diborane. In turn, the borane polymers are easily converted to a variety of other functionalities, under mild reaction conditions. A wide range of telechelic polymers, with various polymer backbones, polymer molecular weight and functionalities, can be produced.

An object of this invention is to develop hydrocarbon polymers having a reactive borane group at chain ends or within the polymer chain.

It is also an object of the invention to develop convenient methods of preparation of polymeric hydrocarbons with reactive terminal borane groups. These and other objects and advantages of the invention will become readily apparent from the following description and are particularly delineated in the appended claims. Advantages of the present invention over the prior art and a better understanding of the invention and its use will become more apparent form the following disclosure wherein are set forth, by way of examples, certain embodiments of the invention.

SUMMARY OF THE INVENTION

In accordance with the present invention, polymers having borane groups at the ends of the polymer chains or in the polymer chains and methods of preparation are presented. The synthesis of such compounds involves an olefin exchange reaction between a unsaturated high molecular weight polymer and a borane monomer. The rapid metathesis reaction breaks the polymer backbone at the double bond location and generates a metal-carbene end group which then reacts with the double bond in the borane monomer. This is the basic reaction to incorporate borane group in the polymer backbone. Depending on the structure of borane monomer, the incorporated borane group can be located at the end of polymer chain or inside the polymer chain. Using a borane monomer with only one olefin causes the resulting polymer to be a telechelic polymer with the borane group located at the end of the polymer chain. The molecular weight of the telechelic polymer, lower than that of the original one, is mainly governed by the double bond concentration in the polymer chain and the mole concentration of borane monomers. By the use of borane monomer with multiple olefin groups, the borane groups are inserted into the polymer backbone and the metathesis reaction resembles a transesterification reaction. The concentration of borane groups in the polymer chain and the spacer between two borane groups can also be controlled by the double bond concentration in the polymer chain and the amount of borane monomer charged in the reaction.

This reaction is applicable to all hydrocarbon polymers with unsaturated double bonds in the polymer backbone. Due to the excellent stability of borane group in the metathesis reaction, most metathesis catalysts can be used without suffering any deactivation and side reactions. In addition, the high solubility of the borane moiety in hydrocarbon solution, due to the covalent nature of B—C bonds, maintains a homogeneous solution which ensures complete reaction in a short reaction time. The resulting borane polymers are very versatile intermediates which are easily converted to a variety of other functional polymer under mild reaction conditions. Both polymer structures, with borane group located at the end or inside the polymer chain, result in similar telechelic polymers. Overall, this synthetic route is very general, not only a simple method to prepare existing telechelic polymers, but also to produce new ones which would otherwise be very difficult to obtain in telechelic forms. The present invention describes a wide range of telechelic polymers, with various polymer backbones, polymer molecular weights and functionalities.

DETAILED DESCRIPTION OF THE INVENTION

The borane monomers which are useful in this invention may be generally categorized by the following formulas:

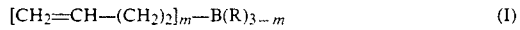

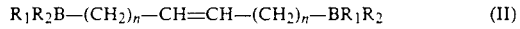

wherein n is an integer ranging from 0 to 12, m is an integer ranging from 1 to 3 and R, $R_1$ and $R_2$ are the alkyl or cycloalkyl radicals having from 1 to 10 carbon atoms. The monomers are generally prepared by simple hydroboration reactions with various dienes and trienes. The monomer (I) is prepared by monohydroboration of $\alpha,\omega$-dienes with dialkylboranes, monoalkylboranes or diborane. Usually, excess diene is used to minimize the dihydroboration products. Preferred dienes are 1,4-pentadiene, 1,5-hexadiene and 1,7-octadiene.

The monomer (II) is prepared by dihydroboration of a triene, containing two $\alpha$-olefins and one internal double bond, with the dialkylboranes which have good hydroboration selectivity at $\alpha$-olefin. The preferred triene is 1,5,9-decatriene and the preferred dialkylborane is 9-borabicyclononane (9-BBN). The hydroboration is preferably conducted at a temperature of from about $-10°$ to $50°$ C. in a suitable solvent, such as tetrahydrofuran (THF), and under an inert gas blanket such as argon or nitrogen. The reaction is performed under mild agitation for a period of at least one hour.

The starting polymer may be any hydrocarbon polymer which contains double bonds in the polymer backbone. The preferred polymers are polydienes, such as 1,4-polybutadiene, 1,4-polyisoprene, polypentenamer, polyoctenamer and polynorbornene, and their copolymers which contain polyolefin structures, such as polyisobutylene, polyethylene, polypropylene, polystyrene, etc. The metathesis catalyst employed in this invention is very general, including both mixed catalysts and Lewis acid free catalysts. It is well known that the metathesis catalyst contains a transition metal of subgroups 4–7 of the Periodic Table, usually titanium, niobium, tantalum, molybdenum, tungsten or rhenium with ligands, such as alkyl, cyclic alkyl, alkylidene, halogen, alkoxy, oxo, imido groups. In the cases of mixed catalysts, the active site of metal carbene is generated by reacting a transition metal with an alkylation agent, containing a metal of main groups 1 through 4. As is known, metathesis catalysts can also contain further activating additives, such as halide, alcohol, epoxide, ether, ester and nitro compounds.

The metathesis olefin exchange reaction takes place by mixing unsaturated polymer and borane monomer together with a metathesis catalyst in an inert organic solvent, such as hexane, toluene, dichloromethane, dichloroethane, nitrobenzene, chlorobenzene, or trichlorobenzene. The reaction usually is very rapid in converting the unsaturated polymer to the corresponding borane containing polymer, even at room temperature. The preferred reaction temperature is between $0°$ to $150°$ C. and the usual reaction time is between 1 minute to 5 hours. With the use of borane monomer (I), m=1 and borane monomer (II), the telechelic polymer was obtained with the borane groups located at both ends of the polymer chain. The molecular structure is shown below:

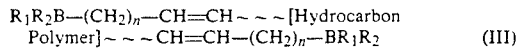

wherein n is an integer range from 0 to 12, and $R_1$ and $R_2$ are the same or different alkyl or cycloalkyl radicals having from 1 to 10 carbon atoms. The preferred hydrocarbon polymers are polydienes, such as 1,4-polybutadiene, 1,4-polyisoprene, polypentenamer, polyoctenamer and polynorbornene, and their copolymers which contain polyolefin structures, such as polyisobutylene, polyethylene, polypropylene, polybutene, polystyrene. In this case, the molecular weight of resulting polymer is lower than that of the original one. The preferred molecular weight is between 300 and 200,000 g/mole, which can be easily controlled by the degree of olefin exchange reaction. Long reaction time and high mole ratio of borane monomer to double bonds in the starting polymer generally give lower molecular weight polymers. On the other hand, with the use of borane monomers (I), m=2 or 3, borane groups become part of polymer chain with the general formula:

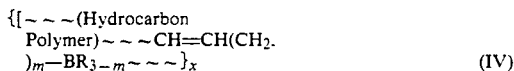
{[~ ~ ~(Hydrocarbon
Polymer)~ ~ ~CH=CH(CH$_2$.
)$_m$—BR$_{3-m}$~ ~ ~]$_x$   (IV)

wherein n is an integer range from 0 to 12, m is 2 or 3 and R is the alkyl or cycloalkyl radicals having from 1 to 10 carbon atoms. The preferred hydrocarbon polymers are polydienes, such as 1,4-polybutadiene, 1,4-polyisoprene, polypentenamer, polyoctenamer and polynorbornene, and their copolymers which contain polyolefin structures, such as polyisobutylene, polyethylene, polypropylene, polybutene, polystyrene. During the olefin exchange reaction, the tungsten carbene catalyst is regenerated at the end of each reaction cycle. Therefore, the same degradation and functionalization reactions continuously take place in catalytic fashion. It is important to note that the catalytic cycles are only possible by eliminating side reactions to the catalyst, particularly catalyst poison by functional groups. Fortunately, borane groups are stable to a broad range of transition metal catalysts.

The borane groups in the polymer (III) and (IV) are readily convertible to other functional groups by reaction with an appropriate reagent under mild reaction conditions to form telechelic polymers (V) having the structure:

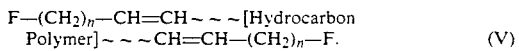
F—(CH$_2$)$_n$—CH=CH~ ~ ~[Hydrocarbon
Polymer]~ ~ ~CH=CH—(CH$_2$)$_n$—F.   (V)

wherein n is an integer ranging from 0 to 12. The preferred hydrocarbon polymers are polydienes, such as 1,4-polybutadiene, 1,4-polyisoprene, polypentenamer, polyoctenamer and polynorbornene, and their copolymers which contains polyolefin structures, such as polyisobutylene, polyethylene, polypropylene, polybutene, polystyrene. F represents the functional groups which can be obtained from the conversion of borane groups. Preferably, F is selected from the group consisting of OH, CHO, NH$_2$ and halogen.

For example, the borane-containing 1,4-polybutadiene, either (III) or (IV), can be oxidized with a mixture of NaOH and peroxide to form "Telechelic" alcohol-terminating 1,4-polybutadiene. Similarly, polymers containing amino functionality may be prepared by reaction of the borane-containing polymer with NH$_2$O-SO$_3$R; polymers containing aldehyde functionality may be prepared by reaction of the borane-containing polymer with a mixture of CO and K(i—C$_3$H$_7$O)$_3$BH; and polymer containing iodine functionality may be prepared by reaction of the borane-containing polymer with a solution of NaI/chloramine-t-hydrate. Other such reactions are disclosed by H. C. Brown, "Organic Synthesis via Boranes," Wiley-Interscience, 1975.

The following examples are offered to illustrate particular embodiments of the invention, but are not intended to be limitative thereof.

EXAMPLE 1

Synthesis of 6-(9-BBN)-1-hexene

This reaction is based on the monohydroboration of 1,5-hexadiene. In an argon filled dry box, 15.092 g (0.124 moles) of 9-BBN (9-borabicyclononane) dimer crystals were dissolved in 100 ml of dry-degassed THF and added dropwise over 2 hours to 44.515 g (0.542 moles) of 1,5-hexadiene. The solution was stirred at room temperature of 5 hours before any unreacted diene and the THF were removed under vacuum. Another 10.754 g (0.088 moles) of 9-BBN were added to the isolated hexadiene and THF solution as before. Again after 5 hours the unreacted diene and THF were removed and the remaining clear oil fractions were combined and distilled under vacuum. The second fraction collected at 68° C. at 11 μmHg was a clear slightly viscous liquid which proved to be pure hexenyl-9-BBN by $^1$H and $^{11}$B NMR. 36.01 g were collected for a 73.1% yield.

EXAMPLE 2

Synthesis of 1,10-di(9-BBN)-5-decene

To enhance the selectivity of hydroboration at α-olefin, the hydroboration reaction of 1,5,9-decatriene was performed at low temperature. Under inert atmosphere, 9-BBN (5.5 g, 45.1 mmol) dissolved in 70 ml of THF solvent was added dropwise to 1,5,9-decatriene (2.837 g, 20.8 mmol), at −10° C. The reaction mixture was stirred at −10°C. for 10 hours, then slowly warmed up to room temperature. To ensure the complete consumption of 9-BBN, the reaction was continued at room temperature for another 2 hours. After removing THF solvent by vacuum distillation, the product was filtered through glass fibres in a dry box to yield 7.51 g (95%) of viscous liquid. The $^1$H NMR study of the product indicates total absence of α-olefin. Based on the peak intensity ratio between the hydrogens located on saturated and unsaturated carbons, the product is a mixture which consists of 82.75% of 1,10-di(9-BBN)-5-decene and trihydroborated product.

EXAMPLE 3

Synthesis of α,ω-di(9-BBN)-1,4-polybutadiene

In an argon filled dry box, 1-hexenyl-6-(9-BBN) (2.83 g) was added to a solution containing cis-1,4-polybutadiene (4.8 g) and toluene (20 ml). The metathesis reaction was started by the addition of 0.33 g of WCl$_6$ and 0.298 g of Sn(Me)$_4$ which were pre-mixed and aged for 5 minutes in 5 ml of toluene. The reaction solution was then continuously stirred at room temperature with a mild vacuum (25 mm Hg) to remove the by-product of ethylene. The viscosity of polymer solution decreased significantly during the reaction process. After certain reaction time, the reaction was terminated by the addition of isopropanol (2 ml). The solution was then subjected to high vacuum to remove toluene, excess isopropanol and unreacted 1-hexenyl-6-(9-BBN). The resulting polymer is α,ω(9-BBN)-1,4-polybutadiene which has lower molecular weight than the starting polymer. As shown in Table I, the molecular wight is inversely related to the reaction time.

TABLE 1

| A Summary of Molecular Weight Changes During Metathesis Reaction of cis-1,4-polybutadiene | | | | |
|---|---|---|---|---|
| Sample | Reaction Time | Mw | Mn | Polydispersity |
| PB | 0 min. | 436,362 | 172,136 | 2.53 |
| PB-A | 8 min. | 82,594 | 39,673 | 2.08 |
| PB-B | 15 min. | 14,070 | 8,073 | 1.74 |
| PB-C | 30 min. | 1,896 | 1,026 | 1.85 |

* Molecular weight calculation was based on the calibration curve of polybutadiene (35% cis, 55% trans and 10% 1,2-isomers).

The molecular weight 1,4-polybutadiene decreased from four hundred thousand to two thousand within a half hour. In the other words, every polymer chain on average was degraded about two hundred times with various metathesis reaction times. It is interesting to note that the molecular weight distribution becomes narrower as the molecular weight decreased. This may indicate that the preference reaction in high molecular weight polymer was taking place in the beginning of the reaction. The reaction was very effective even under mild reaction conditions.

EXAMPLE 4

Synthesis of α,ω-dihydroxy-1,4-polybutadiene

The resulting α,ω-(9-BBN)-1,4-polybutadiene in Example 3 was redissolved in 30 ml of THF for oxidation reaction. This reaction was carried out by adding 2.5 ml of 6N NaOH solution and 4.8 ml of 30% $H_2O_2$ solution. To ensure the complete oxidation, the solution was heated to 45° C. for 3 hours. The procedure to purify the resulting hydroxy polymers was dependent on their molecular weight. For high molecular weight cases, the coagulation of polymer was caused by adding 100 ml of Iospropanol to solution, then standard solution-desolution cycles were applied by further remove the impurities. For the low molecular weight cases, in which the reactions were performed for more than 15 minutes, the final polymer solution was washed with brine solution several times. The THF fraction was collected from a separation funnel. After solvent-removal, the remaining polymer was a viscous light brown liquid which was then subjected to standard silica column chromatography to remove the impurities. The initial elution solvent was nonpolar, such as hexane, followed by a light polar solvent consisting of hexane mixed with diethyl ether. After solvent-removal, all polymer fractions are free of impurities. The recovery of polymer after column fractionation is very high, usually the sum of all fractions is close to 100% yield.

Column chromatography with gradient solvent polarity was also used to fractionalize the polymer mixtures. Table II shows the polymer fractions containing the corresponding hydroxylated product of sample PB-C.

TABLE II

A Summary of Hydroxylated Polybutadiene after Column Fractionation

| Fraction | Solvent (hexane/ether) | Yield (g) | Mn | Mw/Mn | Functionality |
|---|---|---|---|---|---|
| 1 | 100/0 | 0.25 | 399 | 1.32 | <0.1 |
| 2 | 99/1 | 0.568 | 990 | 1.63 | 0.3 |
| 3 | 98/2 | 0.251 | 1135 | 1.86 | ~1 |
| 4 | 95/5 | 0.911 | 1646 | 1.29 | ~1 |
| 5 | 90/10 | 0.768 | 877 | 1.21 | 1.6 |
| 6 | 70/30 | 1.12 | 877 | 1.88 | ~2 |
| 7 | 0/100 | 0.56 | 1048 | 1.87 | ~2 |

The hydroxylated polybutadiene was separated by hexane/ether mixed solvent. Overall, the molecular weight is not much different between each fraction and the molecular weight distribution is slightly reduced from that of the original mixture. On the other hand, the functionality number (number of functional groups in each polymer chain) increases with the increase of solvent polarity. Only a small portion of polymer (18%, fraction 1 and 2) has almost no functional group. The middle portions (26%, fraction 3 and 4) have functionality close to 1. The major portion (56%, the sum of fractions 5 to 7) of polymer has functionality number about , 2

EXAMPLE 5

Synthesis of α,ω-di(9-BBN)-1,4-polybutadiene

A similar degradative metathesis functionalization reaction, as shown in Example 3, was performed in a dry box, except that the borane monomer was 1,10-di(9-BBN)-5-decene from Example 2 and the reaction was performed without the application of vacuum. 1,4-Polybutadiene (1.995 g, Mw=436,362 and MN=172,136) was dissolved in 25 ml of toluene, then mixed with 1.404 g (3.7 mmol) of 1,10-di(9-BBN)-5-decene. The metathesis catalyst was prepared by mixing tungsten hexachloride (147 mg, 0.371 mmol) dissolved in 3 ml of toluene and tetramethyltin (132 mg, 0.738 mmol). The color of tungsten changed from purple to deep red which indicated the generation of metallacarbene active sites. The catalyst was allowed to age for 5 min. before adding to the polymer solution. The metathesis reaction took place with simultaneous degradation and functionalization of 1,4-Polybutadiene backbone. The reaction was proceeded for 30 min., then terminated by the addition of IPA. The reaction flask as sealed off with a valve. Outside the dry box, the reaction mixture was subjected to high vacuum to remove excess IPA and toluene. The resulting viscous liquid is low molecular weight telechelic polymer, α,ω-di(9-BBN)-1,4-polybutadiene with MN=1,222 g/mole and Mw/Mn=2.21. The yield is close to 100%. The functionality is about 2, two 9-BBN groups located at both ends of the polymer chain.

A series of similar reactions have been done by changing the polymer/catalyst and polymer/monomer ratios. The results were easy to be analyzed by their corresponding hydroxylated form, α,ω-dihydroxy-1,4-polybutadiene as shown in Table III. The detail oxidation reactions are shown in Example 6.

TABLE III

A Summary of α,ω-Dihydroxy,1,4-Polybutadiene Prepared by Various Reaction Conditions

| Sample # | Butadiene*/ Catalyst | Butadiene*/ Monomer** | Mn | Mw/Mn | Functionality |
|---|---|---|---|---|---|
| 1 | 100/1 | 6/1 | 1,003 | 1.74 | ~2 |
| 2 | 100/1 | 10/1 | 1,222 | 2.21 | ~2 |
| 3 | 100/1 | 20/1 | 1,203 | 2.38 | ~2 |
| 4 | 250/1 | 6/1 | 4,301 | 2.12 | ~2 |
| 5 | 250/1 | 10/1 | 7,957 | 2.04 | ~2 |

*Butadiene units in 1,4-polybutadiene which has high molecular weight, Mw = 436,362 and Mn = 172,136.
**Monomer is 1,10-di(9-BBN)-5-decene.

The molecular weight was determined by GPC study and functionality was concluded from GPC and $^1H$ NMR results as described in Example 7. The use of borane monomer of 1,10-di(9-BBN)-5-decene eliminates the side reaction (as shown in Example 4) which causes some imperfect chain ends. In addition, the molecular weight of telechelic polymer can be controlled by the catalyst and monomer charged during the reaction.

EXAMPLE 6

Synthesis of α,ω-dihydroxy-1,4-polybutadiene

The α,ω-di(9-BBN)-1,4-polybutadiene polymers in Example 5 were oxidized to α,ω-dihydroxy-1,4-polybutadiene by using $NaOH/H_2O_2$ solution. A continuous nitrogen atmosphere was maintained during the oxidation process. The sample described in Example 5 was dissolved in THF solvent before adding 4 ml of degassed 6N NaOH solution via a syringe. The polymer solution was then stirred and cooled to low temperature in an ice-water bath. About 3 ml of degassed 30% $H_2O_2$ was added dropwise to convert borane to hydroxy groups. To ensure complete oxidation, the reaction mixture was warmed up to 45° C. and allowed to stir for 5 hours. The purification procedure was done by washing the reaction mixture with warm alkali solution twice to remove any water soluble impurities. The THF layer was isolated. After solvent-removal, the viscous liquid was further washed with methanol. The remnant polymer liquid was then subjected to high vacuum to remove the traces of solvents. The final $\alpha,\omega$-dihydroxy-1,4-polybutadiene (1.39 g) was obtained with the corresponding yield of 70%. This telechelic polymer is the sample 2 in Table III.

EXAMPLE 7

Structure studies of $\alpha,\omega$-dihydroxy-1,4-polybutadiene

The molecular weight of the resulting $\alpha,\omega$-hydroxy-1,4-polybutadiene was determined by GPC study. To be able to measure the molecular weight of oligomers, a series of columns (two $10^2$ A, one $5 \times 10^2$ A, one $10^3$ A and one $10^4$ A) were used in GPC measurements. The IR and $^1$H NMR spectra reveal the microstructure of $\alpha,\omega$-hydroxy-1,4-polybutadiene. By comparing the IR spectra of 1,4-polybutadiene and $\alpha,\omega$-hydroxy-1,4-polybutadiene. Two new absorption peaks at 3300 cm$^{-1}$ ($n_{O-H}$) and 1050 cm$^{-1}$ ($n_{C-O}$) are observed, which are due to the hydroxy groups in the functionalized polymer. The same evidence of hydroxyl group in polymer is observed in $^1$H NMR spectrum with a new triplet peak at $\delta = 3.5$ ppm, corresponding to a methylene unit next to a primary hydroxyl group. Combining GPC and $^1$H NMR results, one can theoretically calculate the functionality number and the average number of functional group in each polymer chain.

Thus is described our invention and the manner and process of making and using it in such clear, concise, and exact terms so as to enable any person skilled in the art to which it pertains, or with which it is most nearly connected, to make and use the same.

What is claimed is:

1. A polymer compound having boron atoms located at the ends of polymer chain or in the polymer backbone, wherein the boron containing polymer has a formula consisting of:

$R_1R_2B-(CH_2)_n-CH=CH \sim \sim$ [Hydrocarbon Polymer] $\sim \sim \sim CH=CH-(CH_2)_n-BR_1R_2$ $\{[\sim \sim$ (Hydrocarbon Polymer) $\sim \sim \sim CH=CH(CH_2)_n-]_m-BR_{3-m} \sim \sim \sim\}_x$ or combinations thereof
wherein n is an integer range from 0 to 12, m is 2 or 3, $R_1$ and $R_2$ are the same or different alkyl or cycloalkyl radicals having from 1 to 10 carbon atoms and R is the alkyl or cycloalkyl radicals having from 1 to 10 carbon atoms.

2. A compound according to claim 1, wherein the hydrocarbon polymer is the polydiene, 1,4-polybutadiene, 1,4-polyisoprene, polypentenamer, polyocetenamer or polynorbornene, or the copolymers polyisobutylene, polyethylene, polypropylene, polybutene, or polystyrene.

3. A method for preparing the boron containing polymers of claim 1 comprising reacting unsaturated polymer and borane monomer together with a metathesis catalyst in an inert organic solvent under inert atmosphere or under vacuum.

4. A method according to claim 3 wherein the organic solvent is liquid carbohydron such as hexane, toluene, dichloromethane, dichloroethane, nitrobenzene chlorobenzene or trichlorobenzene.

5. A monomer compound having the following formula:

$[CH_2=CH-(CH_2)_n]_m-B(R)_{3-m}$ $R_1R_2B_n(CH_2)-CH=CH-(CH_2)_n-BR_1R_2$ wherein n is an integer range from 0 to 12, m is an integer range from 1 to 3 and R, $R_1$ and $R_2$ are the alkyl or cycloalkyl radicals having from 1 to 10 carbon atoms.

6. A method according to claim 3 wherein the unsaturated polymer is 1,4-polybutadiene, 1,4-polyisoprene, polypentenamer, polyoctenamer or polynorbornene, or the copolymers polyisobutylene, polyethylene, polypropylene, polybutene, or polystyrene.

7. A method according to claim 3 wherein the metathesis catalyst contains metal carbene active species M=C, where M is a transition metal, which species is generated in situ by reacting a transition metal compound with an alkylating agent in the presence or absence of further activating additives.

8. A method according to claim 7 wherein the transition metal compound contains titanium, niobium, tantalum, molybdenum, tungsten or rhenium and a ligand selected from alkyl, cyclic alkyl, alkylidene, halogen, alkoxy, oxo, or imido groups.

9. A method according to claim 8 wherein the alkylation agent is an organometallic compound containing a metal selected from the periodic table main groups IA-IVA and ligands which comprise an alkyl groups of 1 to 10 carbon and halides as in tetramethyltin or dialkylaluminum chloride.

10. A telechelic polymer, with functional group located at the ends of polymer chain, having the structure:

$F-_n(CH_2)-CH=CH \sim \sim$ [Hydrocarbon Polymer] $\sim \sim \sim CH=CH-(CH_2)_n-F$ wherein n is an integer range from 0 to 12.

11. A polymer compound according to claim 10, wherein the molecular weight is between 300 and 200,000 g/mole as determined by a Water's GPC and narrow molecular weight polystyrene samples as standard.

12. A polymer according to claim 10, wherein the hydrocarbon polymer is the polydiene 1,4-polybutadiene, 1,4-polyisoprene, polypentenamer, polyoctenamer or polynorbornene, or the copolymers polyisobutylene, polyethylene, polypropylene, polybutene, or polystyrene.

13. A process to prepare the telechelic polymers of claim 10 comprising the interconversion reaction of borane groups in borane-containing polymers.

14. A polymer compound according to claim 1, wherein the molecular weight is between 300 and 200,000 g/mole as determined by a Water's GPC and narrow molecular weight polystyrene samples as standard.

15. A compound according to claim 10 wherein the functional groups are OH, CHO, $NH_2$ or halogen.

16. A method according to claim 7 wherein the activating additive usually is a proton donor, such as alkyl or aryl alcohol or epoxide compounds which contain 1 to 20 carbon atoms or other compounds like halide, ether, ester and nitro compounds.

17. A method according to claim 3 wherein the metathesis catalyst is a metal carbene species which is a Lewis acid free catalyst, selected from the group of $W(=CHR)(NAr)OCCH_3(CF_3)_2)_2$, $W(=CHR)NAr)(Ot-Bu)_2$, $Mo=(CHR)(NAr)(OCCH_3(CF_3)_2)_2$ and $Mo(=CHR)(NAr)(Ot-Bu)_2$ where R=t—Bu or $CMe_2Ph$ and Ar=2,6-diisopropylphenyl.

* * * * *